United States Patent
Satake et al.

(10) Patent No.: US 9,285,347 B2
(45) Date of Patent: Mar. 15, 2016

(54) BUBBLE REDUCTION DEVICE, CHROMATOGRAPHY DEVICE, BUBBLE REDUCTION METHOD, AND BUBBLE REDUCTION PROGRAM

(71) Applicants: Seiji Satake, Kyoto (JP); Tokuo Kasai, Kyoto (JP); Akira Sezaki, Kyoto (JP); Takeshi Matsubara, Kyoto (JP)

(72) Inventors: Seiji Satake, Kyoto (JP); Tokuo Kasai, Kyoto (JP); Akira Sezaki, Kyoto (JP); Takeshi Matsubara, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 346 days.

(21) Appl. No.: 13/903,191

(22) Filed: May 28, 2013

(65) Prior Publication Data
US 2013/0319087 A1    Dec. 5, 2013

(30) Foreign Application Priority Data

May 30, 2012 (JP) ................. 2012-123464
Mar. 5, 2013 (JP) ................. 2013-043480

(51) Int. Cl.
*G01N 30/06* (2006.01)
*B01D 15/16* (2006.01)
*G01N 30/26* (2006.01)
*B01D 19/00* (2006.01)
*G01N 30/04* (2006.01)
*G01N 30/20* (2006.01)
*G01N 30/24* (2006.01)
*G01N 30/88* (2006.01)
*B01L 3/00* (2006.01)
*G01N 30/32* (2006.01)

(52) U.S. Cl.
CPC .............. *G01N 30/06* (2013.01); *B01D 15/16* (2013.01); *B01D 19/0036* (2013.01); *B01D 19/0063* (2013.01); *G01N 30/04* (2013.01); *G01N 30/26* (2013.01); *B01L 3/502723* (2013.01); *G01N 30/20* (2013.01); *G01N 30/24* (2013.01); *G01N 2030/322* (2013.01); *G01N 2030/8822* (2013.01)

(58) Field of Classification Search
CPC .... B01D 15/16; B01D 19/00; B01D 19/0063; G01N 30/04; G01N 30/06; G01N 30/14; G01N 30/22; G01N 30/26; G01N 30/28; G01N 30/34; G01N 30/36
See application file for complete search history.

(56) References Cited

U.S. PATENT DOCUMENTS 5,607,581 A    3/1997   Gerner et al.
6,193,783 B1 *  2/2001   Sakamoto .......... B01D 19/0063
                                              95/247

(Continued)

FOREIGN PATENT DOCUMENTS

EP           0489569 A2     6/1992
JP        2007-202277 A     8/2007
JP        2012-215450 A    11/2012

*Primary Examiner* — Peter Macchiarolo
*Assistant Examiner* — Nathaniel Kolb
(74) *Attorney, Agent, or Firm* — Fox Rothschild LLP

(57) ABSTRACT

A bubble reduction device, chromatography device, bubble reduction method and bubble reduction program capable of reducing bubbles in an eluent. Included are a liquid accommodation portion, a liquid supply apparatus, an air layer formation apparatus, a first channel and an evacuation portion. The liquid accommodation portion accommodates a liquid that is to elute an analysis component from a specimen adsorbed to an adsorption portion. The liquid supply apparatus, by operation of a rod pushing up and polling down, sucks and discharges the liquid through an aperture portion of a tube portion, the aperture portion being oriented upward. The air layer formation apparatus forms an air layer in the tube portion. The first channel connects the liquid supply apparatus with the liquid accommodation portion. The evacuation portion is connected to the first channel via a first switching valve and evacuates the air layer through the first channel.

5 Claims, 14 Drawing Sheets

(56) References Cited

U.S. PATENT DOCUMENTS

2004/0262224 A1* 12/2004 Bidlingmeyer ...... B01D 15/327
  210/635
2007/0049864 A1* 3/2007 Hansen .................. A61M 5/30
  604/68
2009/0149743 A1* 6/2009 Barron .................. A61M 5/007
  600/431

* cited by examiner

BUBBLE REDUCTION DEVICE, CHROMATOGRAPHY DEVICE, BUBBLE REDUCTION METHOD, AND BUBBLE REDUCTION PROGRAM

CROSS-REFERENCE TO RELATED APPLICATION

This application is based on and claims priority under 35 USC 119 from Japanese Patent Application No. 2013-043480 filed on Mar. 5, 2013, and No. 2012-123464 filed on May 30, 2012.

TECHNICAL FIELD

The present invention relates to a bubble reduction device, a chromatography device, a bubble reduction method, and a bubble reduction program.

BACKGROUND ART

Analysis devices that analyze components contained in samples include a chromatography device in which analysis components in a sample are adsorbed to an adsorption portion such as a column or the like, an eluent is supplied to the adsorption portion and the analysis components are eluted, and thereafter components in the eluent are analyzed by measurement devices/processes. An example of this kind of chromatography device, in Japanese Patent Application Laid-Open (JP-A) No. 2007-21227, includes a degassing device that degasses an eluent by causing the eluent to flow in a spiral pipe in a low-pressure atmosphere, such that dissolved oxygen in the eluent passes through microscopic holes formed in the spiral tube.

SUMMARY OF INVENTION

Technical Problem

However, bubbles that are produced in a solution by temperature changes or the like may not be thoroughly removed by a degassing device.

In consideration of the situation described above, an object of the present invention is to provide a bubble reduction device, chromatography device, bubble reduction method and bubble reduction program capable of decreasing bubbles in a liquid.

Solution to Problem

A bubble reduction device in accordance with a first aspect of the present invention includes: a liquid accommodation portion that accommodates a liquid that is to elute an analysis component from a specimen adsorbed to an adsorption portion; a liquid supply apparatus that, by operation of a rod pushing up or pulling down, sucks or discharges the liquid through an aperture portion of a tube portion, the aperture portion being oriented upward; an air layer formation apparatus that forms an air layer in the tube portion; a first channel that connects the liquid supply apparatus with the liquid accommodation portion; and an evacuation portion that is connected to the first channel via a first switching valve and that evacuates the air layer through the first channel.

In the bubble reduction device according to the first aspect of the present invention, the liquid that is to elute analysis components in a specimen that have adsorbed to the adsorption portion is accommodated in the liquid accommodation portion. The liquid accommodation portion is connected with the liquid supply apparatus by the first channel. When the rod is pushed up and pulled down, the liquid may be sucked and discharged through the aperture portion of the tube portion that is oriented upward. The air layer is formed in the tube portion of the liquid supply apparatus by the air layer formation apparatus. Thus, bubbles in the liquid sucked into the liquid supply apparatus come into contact with the air layer and are taken into the air layer, and bubbles in the liquid may be decreased.

The evacuation portion that evacuates the air layer through the first switching valve is connected to the first channel. Thus, by operations of the first switching valve switching to the evacuation portion side thereof and the rod pushing up, the air layer in the tube portion into which the bubbles in the eluent liquid have been taken may be evacuated through the evacuation portion.

In a bubble reduction device according to a second aspect of the present invention, in the bubble reduction device according to the first aspect, the air layer formation apparatus includes an atmosphere release valve provided at the first channel, and the air layer is introduced into the tube portion through the first channel by an operation of the rod pushing up or pulling down in a state in which the atmosphere release valve is open.

In the bubble reduction device according to the second aspect, the atmosphere release valve is provided at the first channel. When this atmosphere release valve has been opened, the air layer is introduced into the tube portion through the first channel by an operation of the rod pushing up or pulling down. Thus, the air layer may be formed in the tube portion by a simple operation.

In a bubble reduction device according to a third aspect of the present invention, in the bubble reduction device according to the first aspect or the second aspect, an upper portion inner wall of the tube portion tapers toward the aperture portion, and a distal end portion of the rod is formed in a shape similar to the shape of the upper portion inner wall.

In the bubble reduction device according to the third aspect, the upper portion inner wall of the tube portion tapers toward the aperture portion. Thus, the air layer in the tube portion may be smoothly discharged, and pooling of the air layer in the tube portion may be suppressed. Because the distal end portion of the rod is formed in a similar shape to the upper portion inner wall of the tube portion, the air layer and liquid in the tube portion may be completely discharged.

A chromatography device in accordance with a fourth aspect of the present invention includes: the bubble reduction device according to any one of the first to third aspects; a second channel that is connected to the first channel via a second switching valve, the second channel supplying the liquid discharged from the liquid supply apparatus to the adsorption portion; and an analyzer that analyzes the analysis component in the liquid passed through the adsorption portion.

In the chromatography device according to the fourth aspect of the present invention, an eluent in which bubbles have been decreased by the bubble reduction device is supplied to the adsorption portion through the second channel that is connected to the first channel via the second switching valve. Analysis components in the liquid that has passed through the adsorption portion are analyzed by the analyzer. Thus, any effects of bubbles in the liquid on the analyzer may be suppressed.

A bubble reduction method in accordance with a fifth aspect of the present invention includes: a liquid suction step of sucking a liquid into a tube portion of a liquid supply apparatus from a liquid accommodation portion; an air layer formation step of forming an air layer in the tube portion and taking bubbles in the liquid into the air layer; and an evacuation step of evacuating the air layer in the tube portion through an evacuation portion.

In the bubble reduction method according to the fifth aspect of the present invention, the liquid is sucked from the liquid accommodation portion to the tube portion of the liquid supply apparatus by the liquid suction step, the air layer is formed in the tube portion, by the air layer formation step, bubbles in the liquid come into contact with the air layer in the tube portion, and the bubbles are taken into the air layer. Then, in the evacuation step, the air layer into which the bubbles have been taken is evacuated through the evacuation portion. Thus, bubbles in a liquid may be decreased.

In a bubble reduction method according to a sixth aspect of the present invention, in the bubble reduction method according to the fifth aspect, the liquid suction step includes pulling down a rod at a speed faster than a maximum movement speed of the liquid.

In the bubble reduction method according to the sixth aspect, because the rod is pulled down at a speed faster than the maximum movement speed of the liquid in the liquid suction step, the suction of the liquid is conducted in a low-pressure atmosphere. Therefore, dissolved oxygen in the liquid gasifies and forms bubbles, and is taken into the air layer in the tube portion. Thus, dissolved oxygen in a liquid may be extracted without the provision of a degassing device.

A bubble reduction program in accordance with a seventh aspect of the present invention causes a computer to execute a process including: a liquid suction procedure of causing a liquid supply apparatus to suck a liquid into a tube portion through a first channel from a liquid accommodation portion; an air layer formation procedure of causing an air layer formation apparatus to form an air layer in the tube portion into which the liquid has been socked and causing bubbles in the liquid to be taken into the air layer; and an evacuation procedure of causing the air layer into which the bubbles have been taken to be evacuated through an evacuation portion that is connected to the first channel via a first switching valve.

Advantageous Effects of Invention

With the configurations described above, the present invention may reduce bubbles in a liquid.

DESCRIPTION OF EMBODIMENTS

Figure 1:
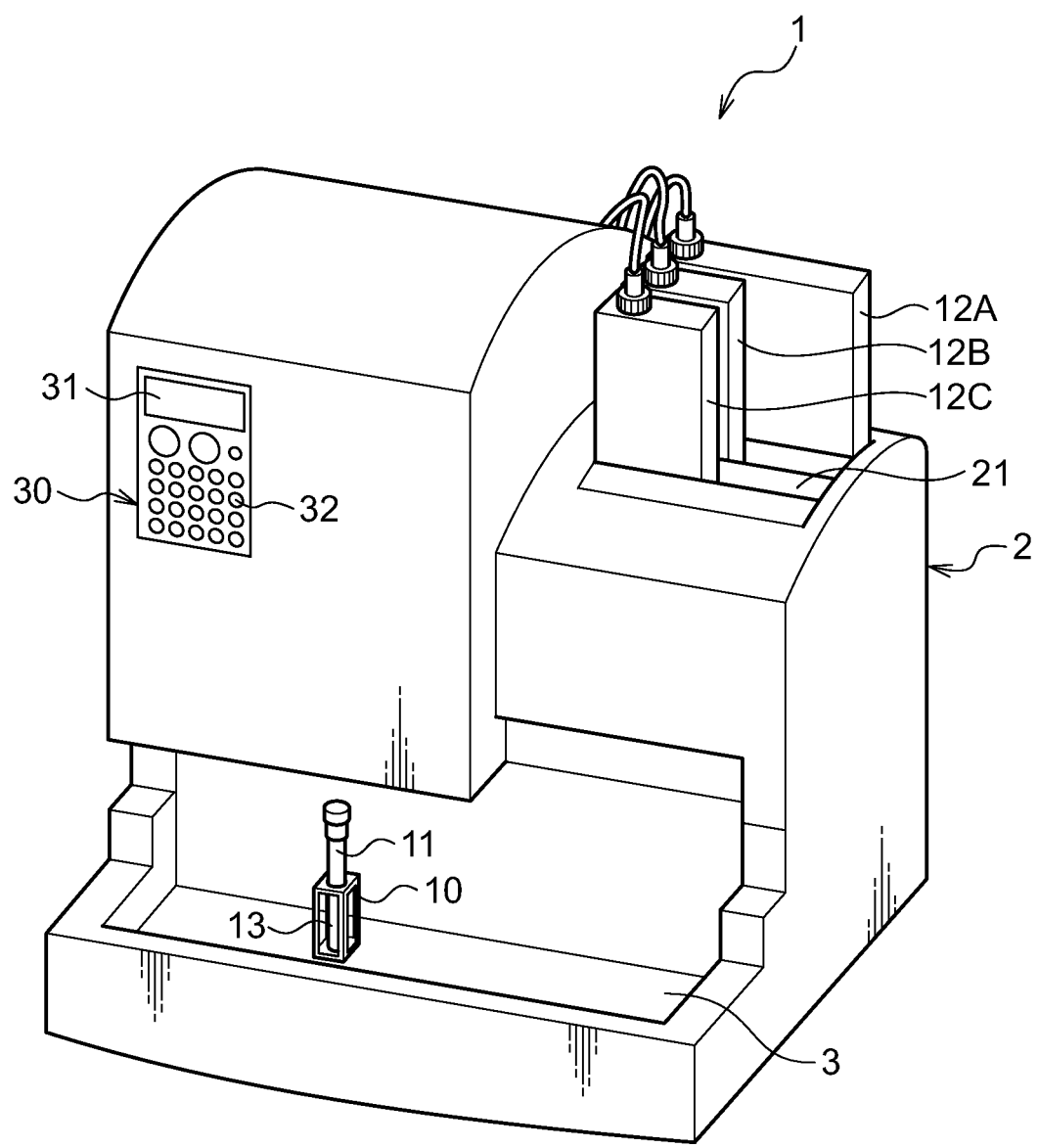
FIG. 1 is a perspective view showing the exterior of a chromatography device that is equipped with a bubble reduction device in accordance with a first exemplary embodiment.

A chromatography device 1 that is equipped with a bubble reduction device 80 according to a first exemplary embodiment of the present invention is described with reference to the attached drawings. The chromatography device 1 according to the present exemplary embodiment is a device that carries out high-performance liquid chromatography (HPLC) completely automatically, which measures glycohemoglobin concentrations in whole blood using a liquid that elutes analysis components (an eluent). As shown in FIG. 1, the chromatography device 1 is equipped with a device main body 2 that serves as a casing. The bubble reduction device 80, a sample preparation unit 4, an analysis unit 5 and the like, which are described below, are accommodated in the device main body 2.

A table 3 is provided at a lower portion of the device main body 2. A rack 10 holding a blood collection tube 11 is placed on the table 3. A specimen 13 is accommodated in the blood collection tube 11. This specimen is a sample of, for example, blood or the like. The present exemplary embodiment has a structure that carries out analysis of a single blood collection tube 11 with a single measurement, but this is not limiting. A rack that holds a plural number of the blood collection tube 11 may be used and successive measurements may be carried out.

A holder portion 21, which is formed of a plural number of recessed portions, is formed at an upper portion at one width direction end side of the device main body 2 (the right side in FIG. 1). In the holder portion 21 are placed, respectively, an eluent pack 12A that serves as a liquid accommodation portion accommodating an eluent A, an eluent pack 12B accommodating an eluent B, and an eluent pack 12C accommodating an eluent C. The eluents accommodated in the eluent packs 12A, 12B and 12C have respectively different pH values and salt concentrations and the like, and are for eluting respective analysis components that have adsorbed to a packing material of a column 60, which is described below. Beside the eluent packs 12, other containers may be placed in the holder portion 21, such as a washing fluid bottle that accommodates a washing fluid for washing piping.

An operation panel 30 is provided at an upper portion of the other width direction end side of the device main body 2. The operation panel 30 includes plural operation buttons 32 and a display screen 31. Analysis conditions and the like may be specified by operation of the operation buttons 32. Analysis results, errors, operation states and the like are displayed at the display screen 31.

Figure 2:
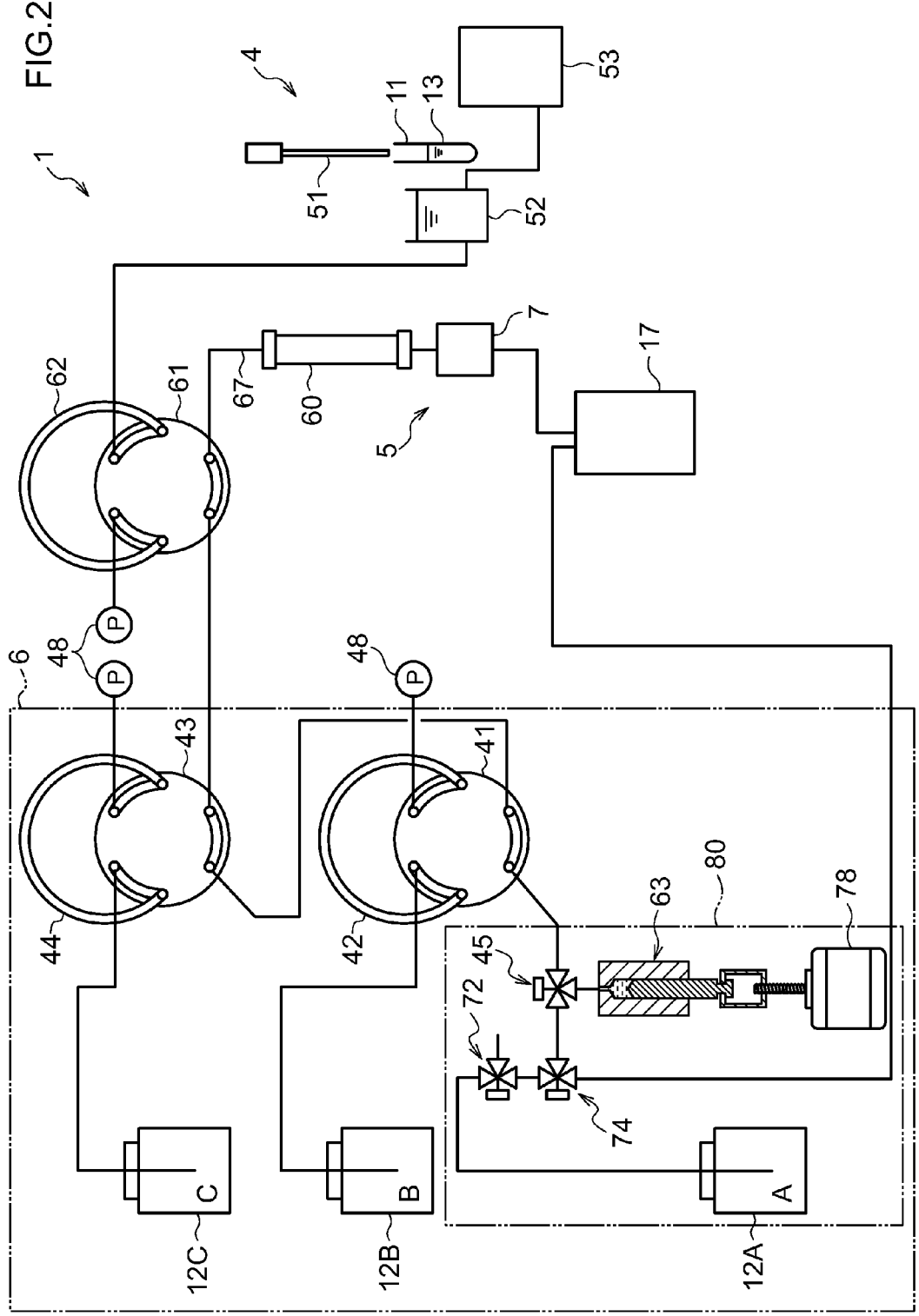
FIG. 2 is a schematic diagram showing internal structures of the chromatography device that is equipped with the bubble reduction device in accordance with the first exemplary embodiment.

As shown in FIG. 2, the chromatography device 1 is principally structured with the sample preparation unit 4, the analysis unit 5 and an eluent liquid supply unit 6 that includes the bubble reduction device 80. The sample preparation unit 4 is a unit that prepares the specimen 13 to be supplied to the analysis unit 5. The sample preparation unit 4 is equipped with a nozzle 51 that sucks up the sample (blood) 13 and a diluent tank 52 that prepares a blood specimen. At an appropriate timing, the blood specimen is supplied from the sample preparation unit 4 to the column 60 via a switching valve 61.

The analysis unit 5 is a unit that measures a concentration of glycohemoglobin in the blood specimen. The analysis unit 5 is equipped with the column 60 and a photometry section 7, which serves as an analyzer. The column 60 is a tube into which the packing material that adsorbs the glycohemoglobin in the blood specimen is packed. The column 60 is formed of glass, stainless steel or resin. In the present exemplary embodiment, as an example, the column 60 that is used is made of stainless steel. The photometry section 7 is a section that shines light onto the eluent passed through the column 60, and optically detects and analyzes hemoglobin from the wavelengths of light that is transmitted. The photometry section 7 is structured with a light source and a light detection unit or the like.

The eluent liquid supply unit 6 is a unit that sucks eluent from the eluent packs 12A, 12B and 12C and supplies the eluent to the column 60 of the analysis unit 5. The eluent liquid supply unit 6 is structured with the eluent packs 12A, 12B and 12C, a plunger pump 63 that serves as a liquid supply apparatus, switching valves 41 and 43, and piping.

The plunger pump 63 sucks the eluent A from the eluent pack 12A and supplies the eluent A at a constant rate. The switching valves 41 and 43 are connected to the eluent packs 12B and 12C. Pumps 48 are connected to the switching valves 41 and 43. If the pumps 48 are operated in the state shown in FIG. 2, the eluents B and C are supplied to loop pipes 42 and 44, respectively. By the switching valves 41 and 43 being switched as appropriate, the eluent B and the eluent C can be supplied to the column 60 rather than the eluent A supplied from the plunger pump 63.

Figure 11:
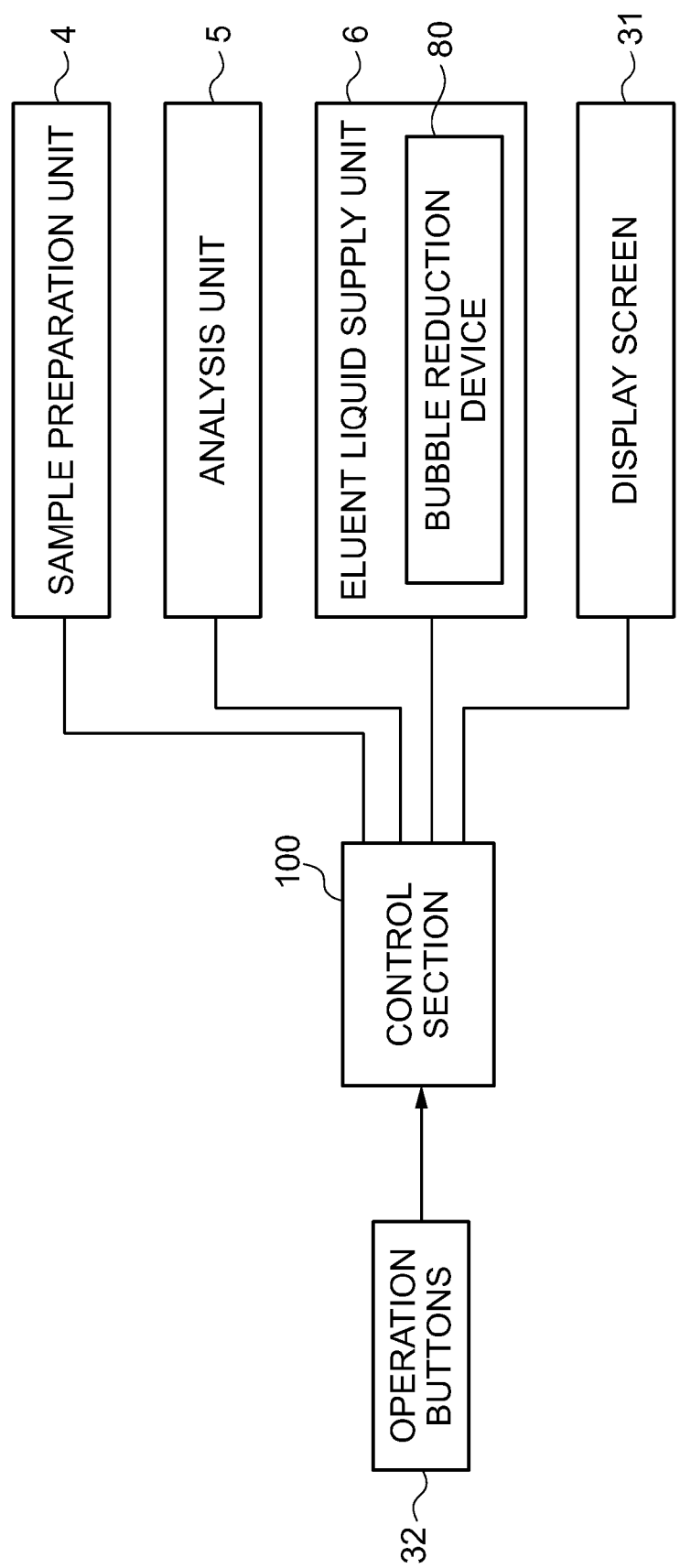
FIG. 11 is a block diagram showing structures of a chromatography device.

As shown in FIG. 11, the chromatography device 1 is equipped with a control section 100. The control section 100 is a computer structured with a CPU that controls the device as a whole, a ROM that stores a program and the like, a RAM that temporarily saves measurement results, and an input/output port. The program is executed in accordance with instructions inputted from the operation buttons 32 and a keyboard (not shown in the drawings) or the like. The control section 100 is electronically connected to the sample preparation unit 4, the analysis unit 5, the eluent liquid supply unit 6 including the bubble reduction device 80, and the display screen 31. The control section 100 instructs the respective units in accordance with the program being executed, and conducts automatic analysis.

In the chromatography device 1 according to the present exemplary embodiment, the sample preparation unit 4, the analysis unit 5, and the eluent liquid supply unit 6 including the bubble reduction device 80 are provided inside the device main body 2 that serves as a casing, but this is not limiting. These may be structured as respectively separate units, in which case the units may be caused to function as a single system by being connected.

Figure 4:
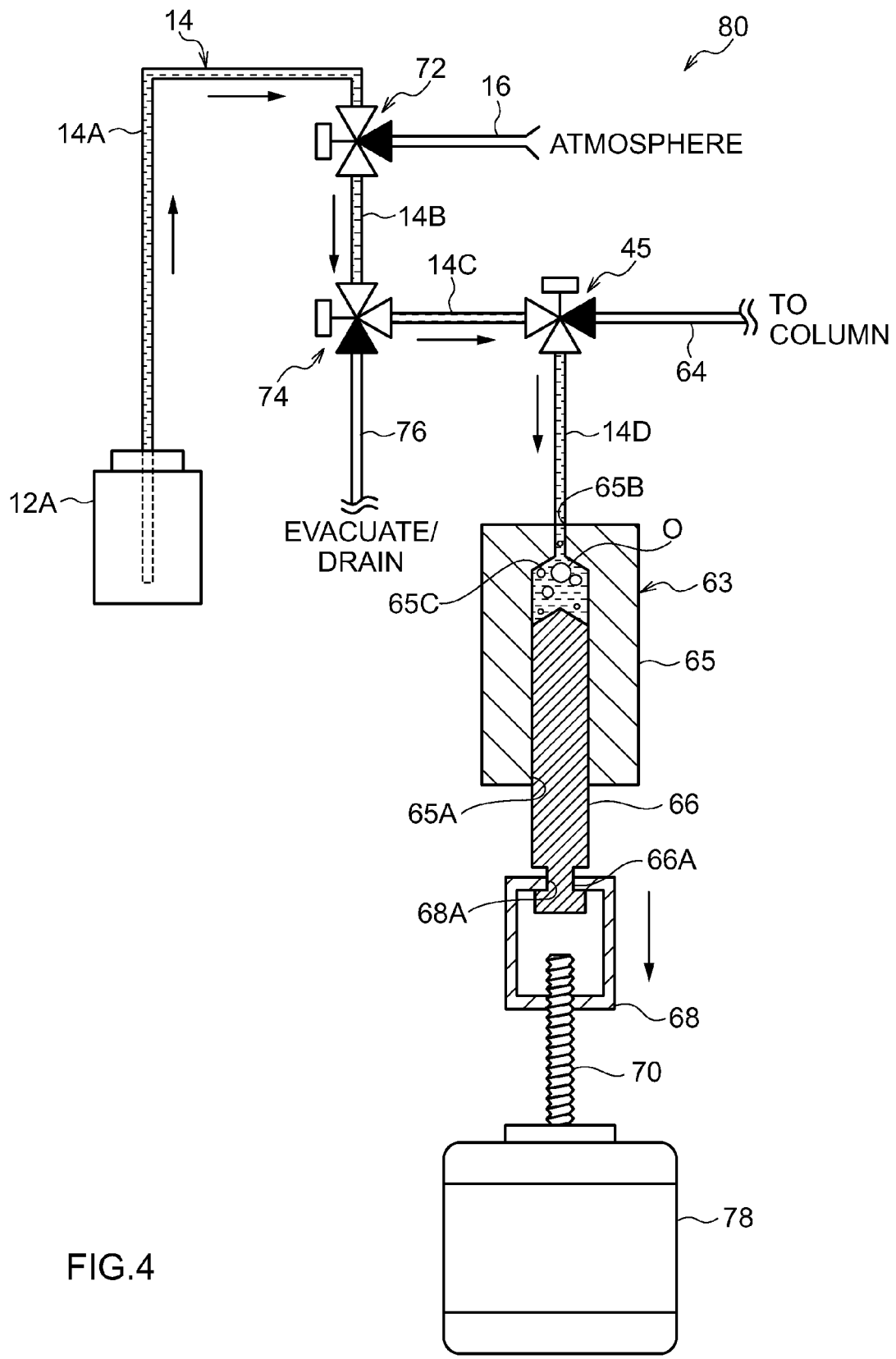
FIG. 4 is an enlarged diagram of principal portions, showing a state in which air is being sucked into a plunger pump that structures the bubble reduction device in accordance with the first exemplary embodiment.

Now, the structure of the bubble reduction device 80 according to the present exemplary embodiment is described. As shown in FIG. 4, the bubble reduction device 80 includes the plunger pump 63, the eluent pack 12A, a first channel 14 that connects the plunger pump 63 with the eluent pack 12A, an atmosphere release valve 72 that serves as an air layer formation apparatus provided at the first channel 14, and an evacuation pipe 76 that serves as an evacuation portion connected to the first channel 14 via a first switching valve 74.

The plunger pump 63 is provided with a syringe 65, which serves as a tube portion. The syringe 65 is a tubular body made of stainless steel, of which upper and lower end portions are open. An inner wall with a constant diameter is formed from an aperture 65A at the lower end side of the syringe 65 to an upper portion of the same. An upper portion inner wall 65C of the syringe 65 forms a taper surface that tapers upward toward an aperture portion 65B. The aperture portion 65B is connected to a pipe 14D. The meaning of the term "upward" as used herein is not limited to a perpendicularly upward orientation. For example, modes in which the syringe 65 is disposed at an angle and the aperture portion 65B is formed diagonally upward are to be encompassed. The syringe 65 may be formed of a metal other than stainless steel, and may be formed of a resin.

A plunger 66 is disposed at the inside of the syringe 65. The plunger 66 serves as a rod that is movable in the up-and-down direction. An outer diameter of the plunger 66 is substantially the same as an inner diameter of the syringe 65, and the plunger 66 slides along the inner periphery face of the syringe 65. An upper end portion of the plunger 66 is formed in a conical shape similar to that of the upper portion inner wall 65C of the syringe 65. The plunger 66 is designed so as to be in area contact with the syringe 65 when the plunger 66 is pushed up to the upper end side, without a gap between the syringe 65 and the plunger 66. An O-ring is attached to the plunger 66, such that fluids inside the syringe 65 do not leak from the aperture 65A.

An annular groove 66A is formed at a lower end portion of the plunger 66. An attachment hole 68A is formed in an upper face of a plunger retention member 68. An aperture edge of the attachment hole 68A engages with the annular groove 66A. A ball screw 70 is threaded into a lower face of the plunger retention member 68, and is connected to a rotary shaft of a motor 78.

Figure 3:
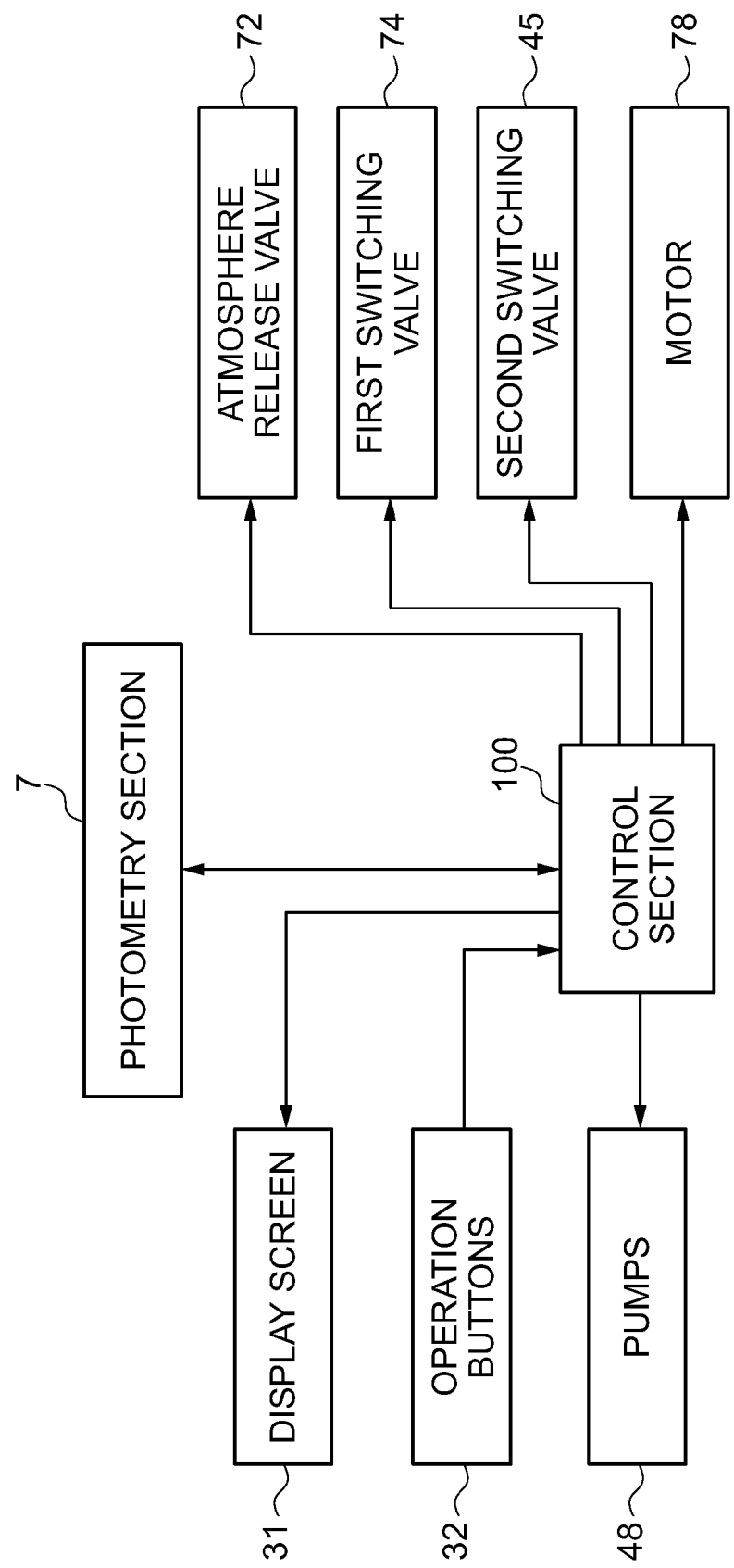
FIG. 3 is a block diagram for describing a control section in accordance with the first exemplary embodiment.

As shown in FIG. 3, the motor 78 is electronically connected to the control section 100. When the control section 100 drives the motor 78, as shown in FIG. 4, the ball screw 70 rotates, the plunger retention member 68 moves in the up-and-down direction and moves the plunger 66, and space inside the syringe 65 is increased or reduced. In the present exemplary embodiment, a stepper motor is used as an example of the motor 78, but this is not limiting and a servo motor or the like may be used.

The first channel 14 that connects the eluent pack 12A with the plunger pump 63 is structured by pipes 14A, 14B, 14C and 14D. The atmosphere release valve 72 is provided between the pipe 14A and the pipe 14B. A ventilation pipe 16, which is opened to the atmosphere, is connected to the atmosphere release valve 72.

In the present exemplary embodiment, a solenoid valve (a three-way valve) that is driven by a solenoid is used as the atmosphere release valve 72. The channel structured by the piping may be switched by the atmosphere release valve 72.

The first switching valve 74, formed of a solenoid valve with the same structure as the atmosphere release valve 72, is provided between the pipe 14B and the pipe 14C. The evacuation pipe 76 is connected to the first switching valve 74. The evacuation pipe 76 extends to a waste liquid tank 17.

The pipe 14C and the pipe 14D are connected by a second switching valve 45. The pipe 14D is connected to the aperture portion 65B of the syringe 65. Piping 64 is also connected to the second switching valve 45. The piping 64 structures a second channel leading to the column 60.

The atmosphere release valve 72, the first switching valve 74 and the second switching valve 45 are electronically connected with the control section 100, and are driven by instructions from the control section 100.

Figure 12:
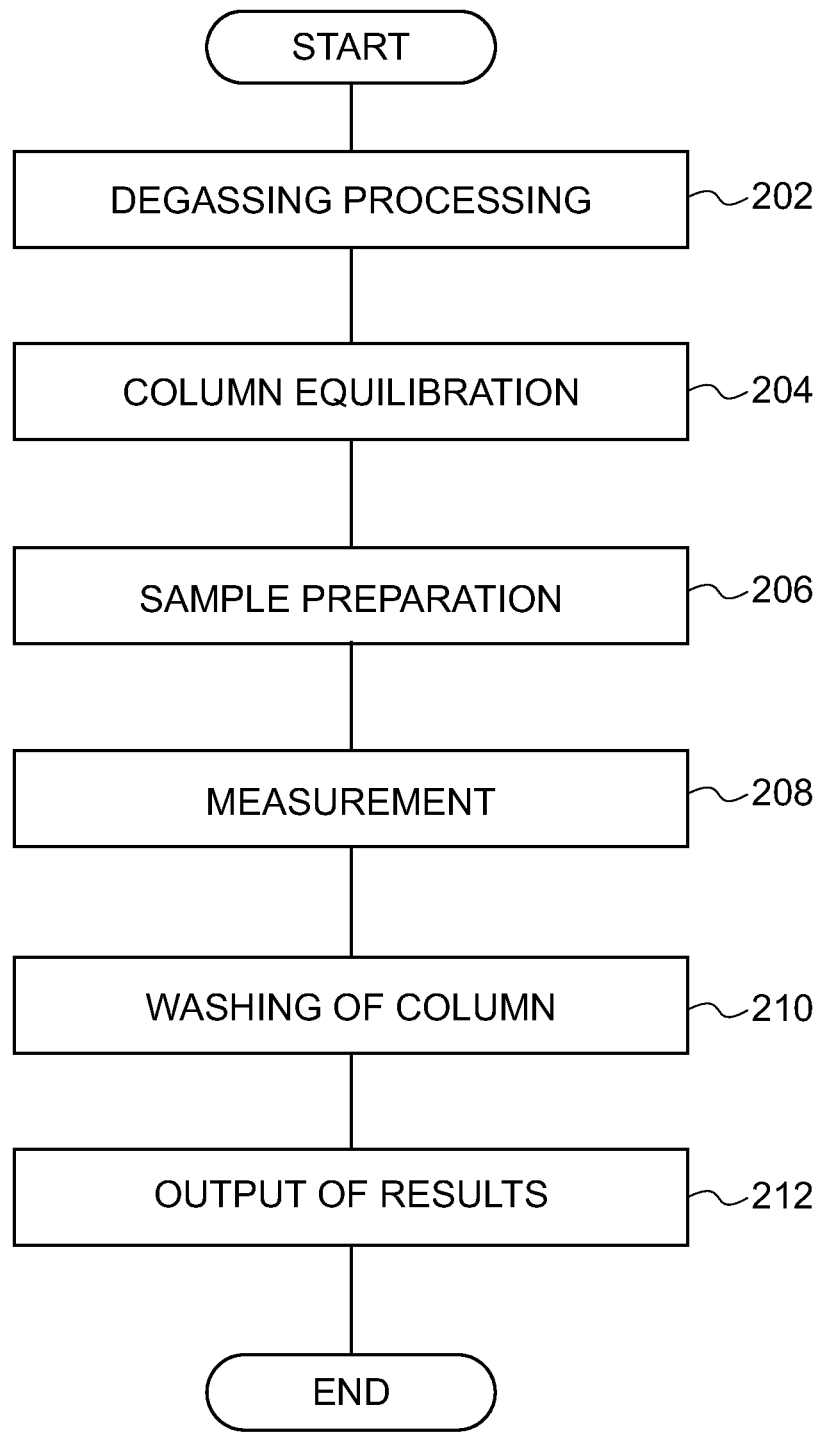
FIG. 12 is a flowchart for describing an automatic analysis process at the chromatography device.

Now, a procedure of automatic analysis by the chromatography device 1 according to the present exemplary embodiment is described in accordance with the block diagram of FIG. 11 and the flowchart of FIG. 12. The automatic analysis herebelow is chromatography that analyzes analysis components contained in a sample of blood or the like. First, when a user operates the operation panel 30 or instructs the control section 100 to start the chromatography device 1 from a keyboard external to the device, the control section 100 executes an automatic analysis program. In a first step 202, the control section 100 controls the bubble reduction device 80 and carries out degassing processing. In the present exemplary embodiment, because the degassing processing is carried out before measurements are taken, dissolved oxygen in an eluent may be removed and generation of noise at the photometry section 7 may be suppressed.

Then, in step 204, the control section 100 controls the eluent liquid supply unit 6 and applies equilibration to the column 60. Here, the equilibration is performed by the eluent A flowing into the column 60 until the packing material of the column 60 is smoothly coated. Specifically, the degassed eluent A that has been sucked up by the plunger pump 63 of the eluent liquid supply unit 6 is pushed out and supplied to the column 60. A duration for which the eluent A flows is set in advance in accordance with the type of column 60.

When the equilibration of the column 60 is complete, the control section 100 proceeds to step 206. In step 206, the control section 100 controls the sample preparation unit 4 and prepares a sample. Specifically, as shown in FIG. 2, the nozzle 51 of the sample preparation unit 4 sucks the specimen 13 from the blood collection tube 11 and drops the specimen 13 into the diluent tank 52. The specimen 13 is diluted in a preparation fluid in a preparation fluid tank 53 in the diluent tank 52, and is supplied to a loop pipe 62 of the switching valve 61 by the pump 48.

In step 208, the control section 100 controls the analysis unit 5 and conducts measurements. The photometry section 7 starts the analysis in response to instructions from the control section 100. The eluent A is supplied to the column 60 for a certain duration. Then, the switching valve 61 is operated and switches the channel of the eluent A, and the specimen 13 in the loop pipe 62 is pushed out with the eluent A and supplied to the column 60.

Analysis components in the specimen are adsorbed to the packing material of the column 60, and the residue of the specimen passes through the photometry section 7 and is drained to the waste liquid tank 17. Thereafter, the eluent A elutes a portion of the analysis components that have adsorbed to the packing material of the column 60, and is supplied to the photometry section 7. The photometry section 7 detects the analysis component(s) in the eluent A and sends data thereof to the control section 100.

When the elution of analysis components by the eluent A is completed, the switching valve 43 switches and alters the flowpath of the eluent A. Hence, the eluent C that has been supplied to the loop pipe 44 by the pump 48 is pushed out by the eluent A and supplied to the column 60. The eluent C elutes analysis components that have not been eluted by the eluent A, and passes through the photometry section 7.

When the elution of analysis components by the eluent C is completed, the switching valve 41 switches and alters the flowpath of the eluent A. Hence, the eluent B that has been supplied to the loop pipe 42 by the pump 48 is pushed out by the eluent A and supplied to the column 60. The eluent B elutes analysis components that have not been eluted by the eluents A and C, and passes through the photometry section 7.

Analysis components in a blood specimen are separated out as described above and subjected to qualitative and quantitative analyses. In the present exemplary embodiment, the chromatography device 1 has a structure that performs automatic analysis when the chromatography device 1 is started, but this is not limiting; analyses may be conducted manually. In this case, a user performs operations to give instructions to switch valves and the like at arbitrary timings.

When measurements are completed, the control section 100 proceeds to step 210. In step 210, the control section 100 controls the eluent liquid supply unit 6 and implements washing of the column 60. Specifically, the eluent A is supplied to the column 60, analysis components that have adsorbed to the packing material of the column 60 are washed away, and equilibration is applied.

Finally, in step 212, the analysis data sent from the photometry section 7 to the control section 100 is collected and outputted in the form of analysis results. The analysis results are displayed at the display screen 31 or a separate monitor or the like. If a successive sample is to be analyzed, this analysis is performed by the same procedure, starting from the degassing processing in step 202.

Figure 8:
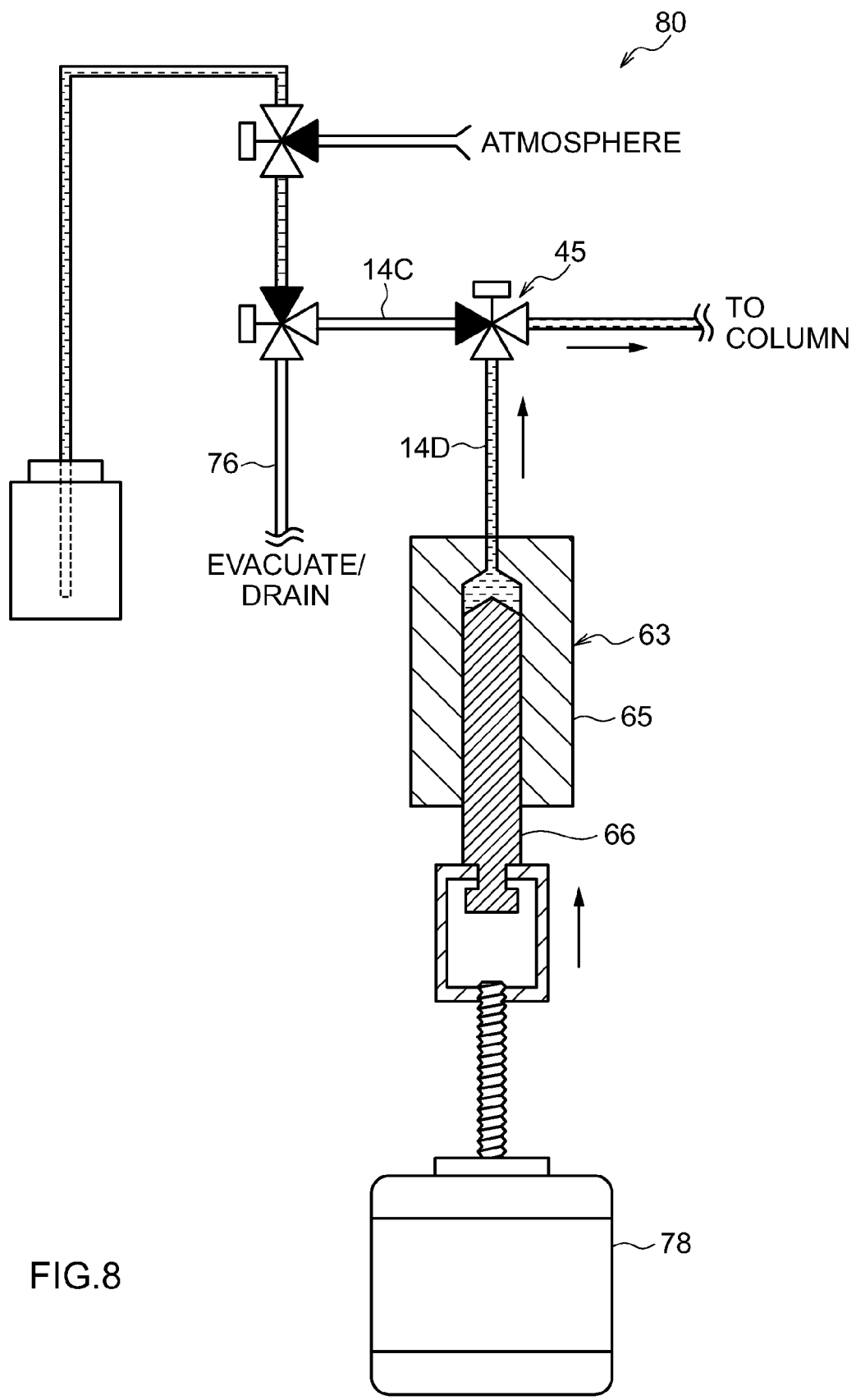
FIG. 8 is an enlarged diagram of principal portions, showing a state in which the eluent is being supplied from the plunger pump that structures the bubble reduction device in accordance with the first exemplary embodiment.
Figure 9:
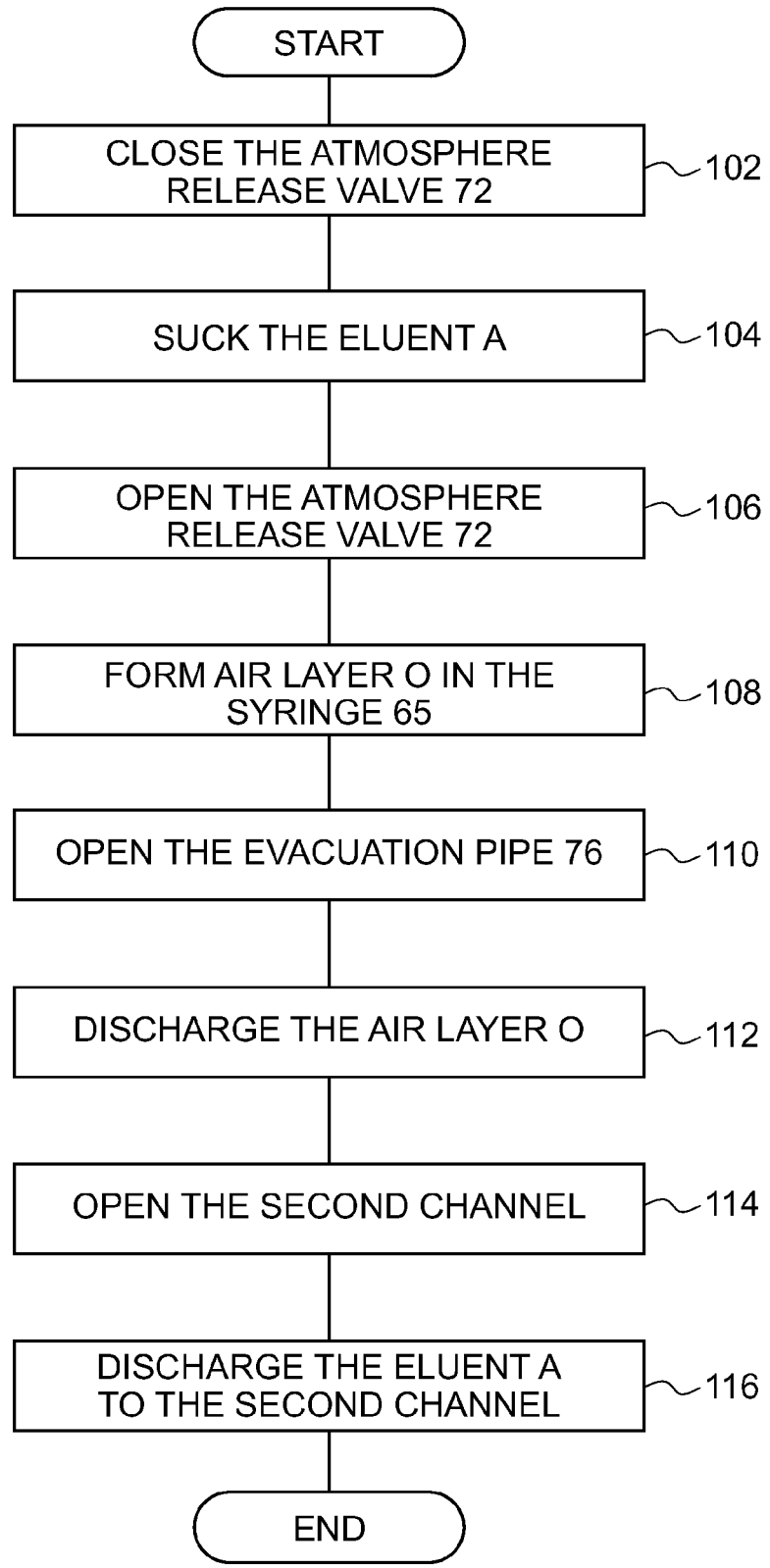
FIG. 9 is a flowchart for describing a procedure of liquid supply by the plunger pump that structures the bubble reduction device in accordance with the first exemplary embodiment.

Now, a bubble reduction method and liquid supply procedure of the eluent A at the bubble reduction device 80 is described in accordance with the flowchart in FIG. 9. In FIG. 4 to FIG. 8, where appropriate for description, solenoid valves that are open are shown white and solenoid valves that are closed are shown as solid black. Firstly, in step 102 of FIG. 9, the control section 100 closes the atmosphere release valve 72 and puts the pipe 14A into fluid communication with the pipe 14B.

Then, in step 104, as shown in FIG. 4, the control section 100 drives the motor 78 of the plunger pump 63, and the plunger 66 is pulled down and sucks the eluent A into the syringe 65 (a liquid suction step/liquid suction procedure). At this time, the control section 100 controls the driving speed of the motor 78 to pull the plunger 66 down faster than a maximum movement speed of the eluent A. Thus, the volume of the interior of the plunger pump 63 is increased and, in accordance with Boyle's law, pressure falls in correspondence with the increase in volume, producing a low-pressure atmosphere. As a consequence, dissolved oxygen in the eluent A gasifies and forms bubbles.

Figure 5:
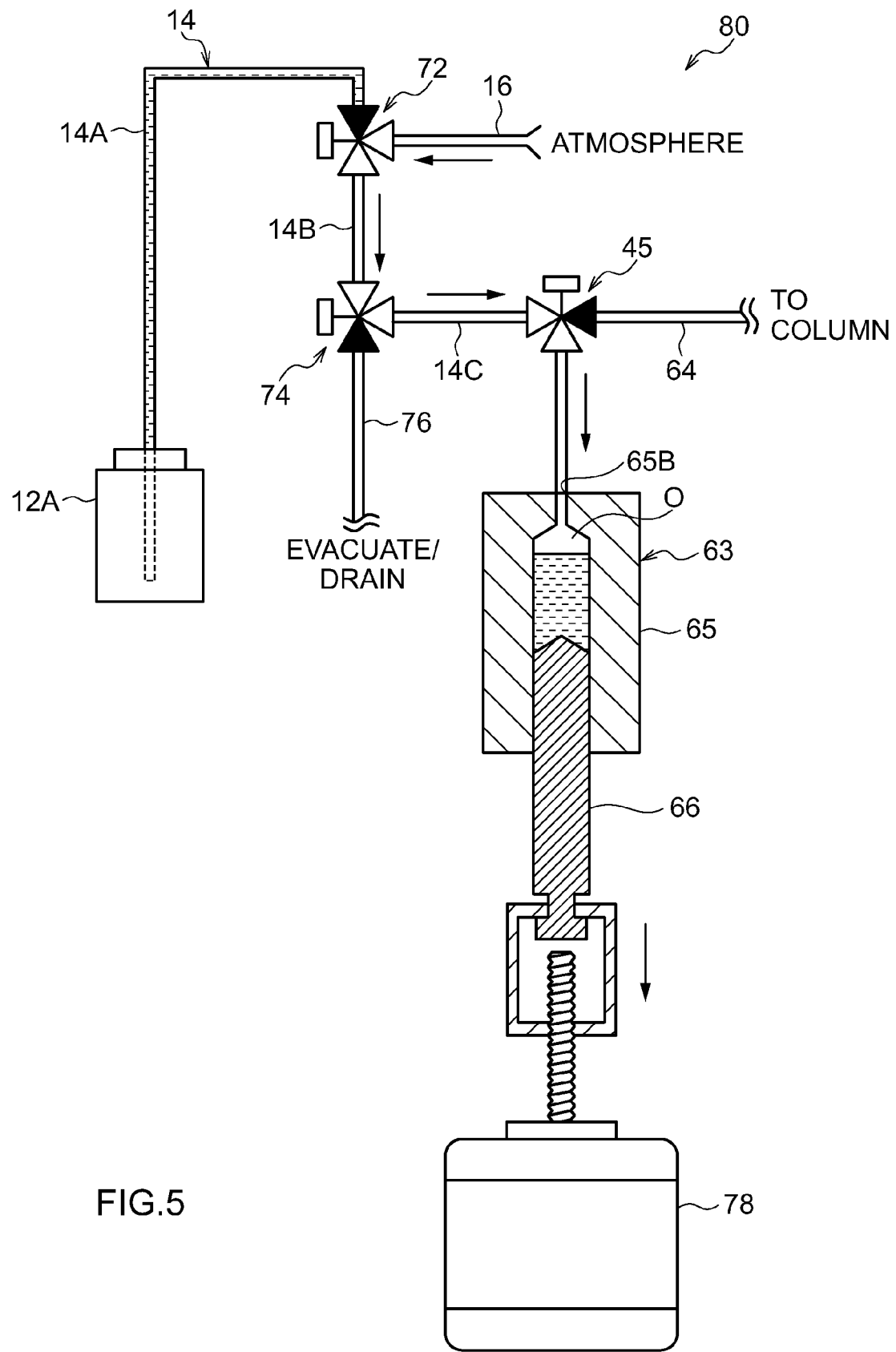
FIG. 5 is an enlarged diagram of principal portions, showing a state in which an eluent is being sucked into the plunger pump that structures the bubble reduction device in accordance with the first exemplary embodiment.

In step 106 of FIG. 9, the control section 100 opens the atmosphere release valve 72 and, as shown in FIG. 5, puts the ventilation pipe 16 into fluid communication with the pipe 14B. In step 108, air is sucked through the ventilation pipe 16, the pipe 14B, the pipe 14C and the pipe 14D, and an air layer O is formed in the syringe 65 (an air layer formation step/air layer formation procedure). If the pipes 14B, 14C and 14D have been filled with the eluent A, some of the eluent A is sucked in together with the air. However, this is not a problem for formation of the air layer O.

The size of the air layer O formed in the syringe 65 is not particularly limited; it is sufficient that it be a size with which bubbles in the liquid can be properly taken into the air layer O. In the present exemplary embodiment, the air is sucked in by the plunger 66 being pulled down. However, a structure is possible in which the air is sucked in by an operation of the plunger 66 pushing up.

Figure 6:
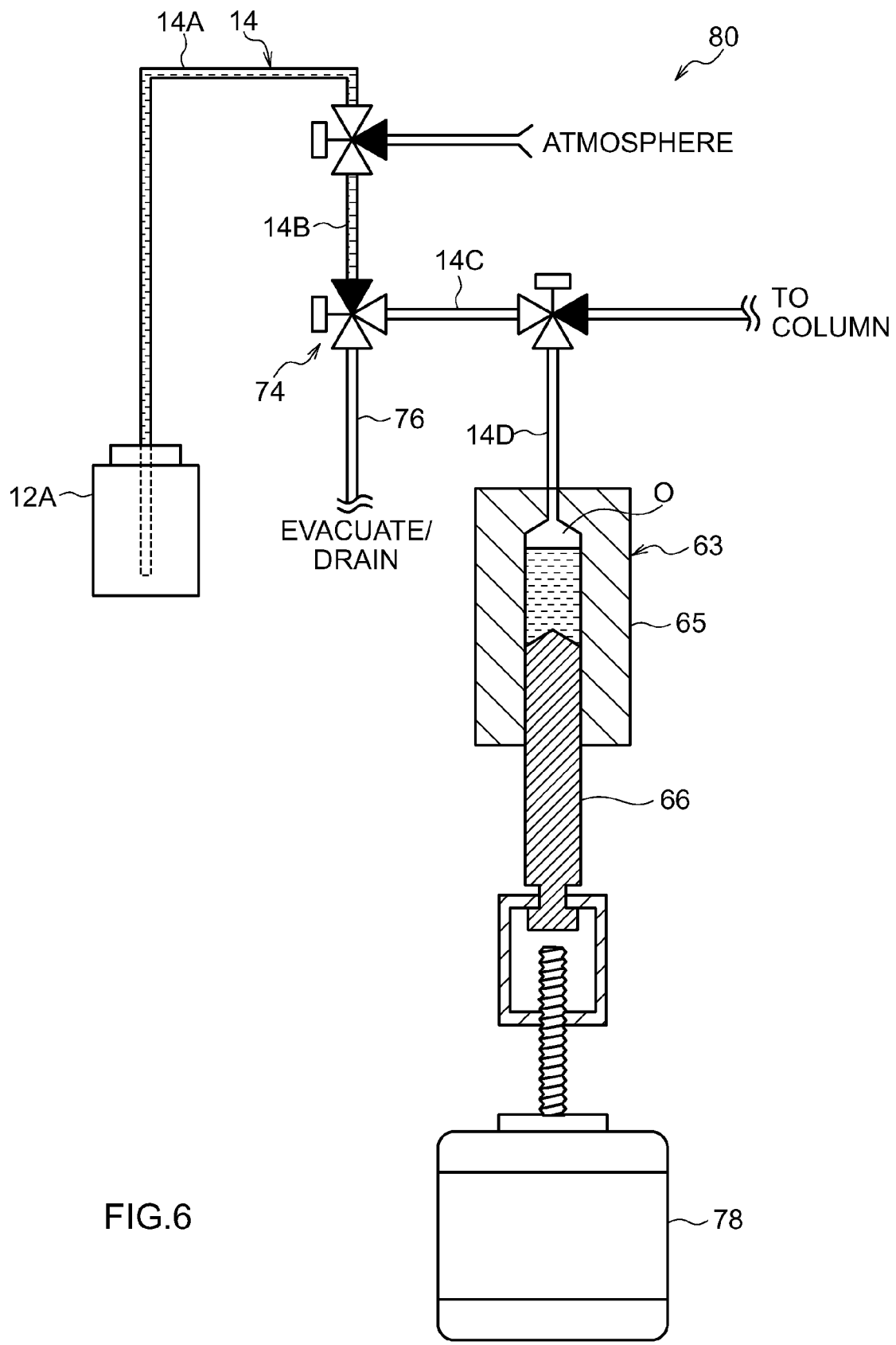
FIG. 6 is an enlarged diagram of principal portions, showing a state in which air in the eluent sucked into the plunger pump that structures the bubble reduction device in accordance with the first exemplary embodiment is collected.

The bubbles into which the dissolved oxygen gasifies as mentioned above and bubbles that were originally present in the eluent A are taken into the air layer O formed in the syringe 65. After a certain amount of the eluent A has been sucked in, the pulling-down operation of the plunger 66 stops and the suction of the eluent A stops. The bubbles collect in an upper portion of the syringe 65, and combine with the air layer O. Then, in step 110, as shown in FIG. 6, the control section 100 operates the first switching valve 74 and puts the pipe 14C into fluid communication with the evacuation pipe 76.

Figure 7:
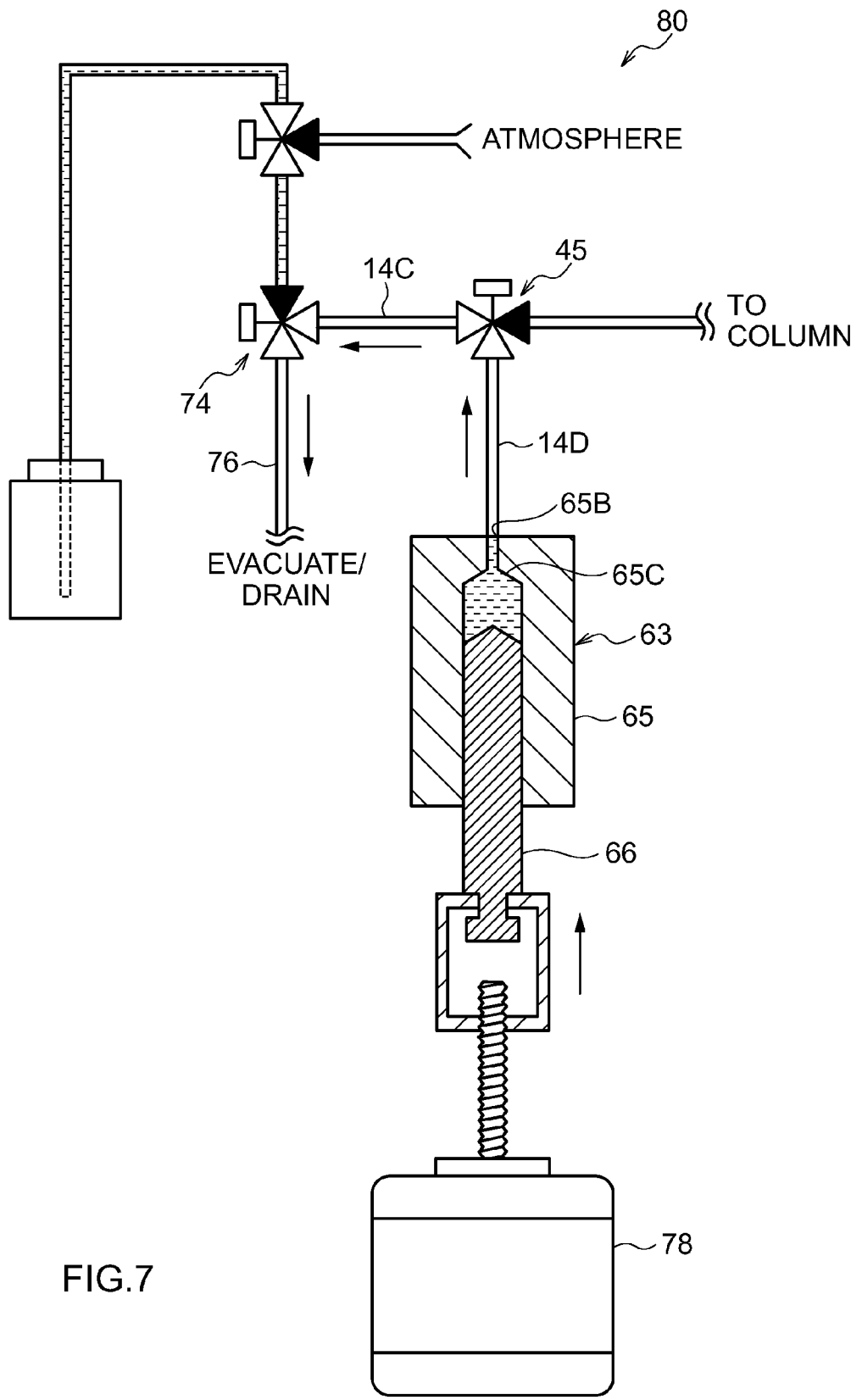
FIG. 7 is an enlarged diagram of principal portions, showing a state in which an air layer is being discharged from the plunger pump that structures the bubble reduction device in accordance with the first exemplary embodiment.

In step 112, as shown in FIG. 7, the control section 100 drives the motor 78 of the plunger pump 63 to push up the plunger 66, and the air layer O in the syringe 65 is evacuated to the waste liquid tank through the pipe 14D, the pipe 14C and the evacuation pipe 76 (an evacuation step/evacuation procedure). If the speed at which the plunger 66 is pushed up at this time is too fast, the air layer O may rise in pressure and bubbles may be taken into the eluent A. Therefore, it is preferable if the plunger 66 is pushed up at a speed lower than the speed at which it was pulled down.

Further, when the air layer O is evacuated, because the shape of the upper portion inner wall 65C of the syringe 65 is formed as a taper toward the aperture portion 65B, the air layer O is not broken up but is evacuated smoothly without remaining in the syringe 65. After the air layer O is evacuated, the plunger 66 is pushed up further and some of the eluent A in the plunger pump 63 is discharged. Thus, the air layer O in the plunger pump 63 is assuredly evacuated. In the present exemplary embodiment, the control section 100 pushes the plunger 66 up to a predetermined position. However, a method is possible in which a sensor or the like detects when the air layer O in the syringe 65 has been completely evacuated and stops the plunger 66.

Thus, the degassing of the eluent A is completed. Then, in step 114 of FIG. 9, the control section 100 operates the second switching valve 45 and, as shown in FIG. 8, puts the pipe 14D into fluid communication with the piping 64 and opens the second channel. Thereafter, in step 116, the motor 78 of the plunger pump 63 is driven and the plunger 66 is pushed up, supplying the eluent A in the syringe 65 to the column 60.

Now, as shown in FIG. 2, the chromatography device 1 according to the present exemplary embodiment has a structure that only degasses the eluent A accommodated in the eluent pack 12A, but this is not limiting. As appropriate, the switching valves may be switched and the eluent packs 12B and 12C may be similarly degassed by the plunger pump 63. Further, respective pumps the same as the plunger pump 63 may be connected to the eluent packs 12B and 12C and all of the eluents may be degassed.

In the present exemplary embodiment, first the eluent A in the syringe 65 is sucked in, then the atmosphere release valve 72 is opened and the air layer O is formed in the syringe 65, but this is not limiting. The air layer O may be formed in the syringe 65 first and then the eluent A sucked in. However, if the air layer O is formed first, the air layer O may expand in the syringe 65 and it may not be possible to suck in a sufficient amount of the eluent A. Moreover, it is more difficult to lower the pressure in the plunger pump 63 when sucking in the eluent A. Therefore, sucking the eluent A in first is more preferable. Furthermore, if the air layer O is formed last, tiny bubbles that adhere to peripheral edges of the distal end portion of the plunger 66 while the eluent A is being sucked in may be taken into the air layer O and removed.

If there are no restrictions on time, the air layer O may be formed in advance in the syringe 65, and when the eluent A is sucked in, the gasified dissolved oxygen comes into contact with and easily combines with the air layer O. Therefore, evacuation is easier.

As described above, the chromatography device 1 according to the present exemplary embodiment is equipped with the bubble reduction device 80, so bubbles in the eluent A may be reduced and the eluent A may be supplied. Further, the speed at which the plunger 66 is pulled down is adjusted to suck in the eluent A in a low-pressure atmosphere. Therefore, dissolved oxygen in the eluent A may be gasified and taken into the air layer more easily.

In an ordinary degassing device, an eluent flows in a spiral pipe in a low-pressure atmosphere and dissolved oxygen in the eluent passes through microscopic holes formed in the spiral pipe. In consequence, bubbles in the eluent may not be adequately removed. In contrast, in the bubble reduction device 80 according to the present exemplary embodiment, the air layer O formed in the syringe 65 and the bubbles come into contact and collect at the upper portion, so bubbles in the eluent may be decreased. In particular, if the eluent is stored in a location with a low temperature, an amount of oxygen dissolved in the eluent is larger than if the eluent were at room temperature. Therefore, if the eluent is simply transferred to a location with a higher temperature, the dissolved oxygen in the eluent gasifies and forms bubbles, and accurate analysis is difficult. In contrast, because the chromatography device 1 according to the present exemplary embodiment may reduce bubbles in the eluent, the effects of bubbles on analysis results may be reduced.

Figure 10:
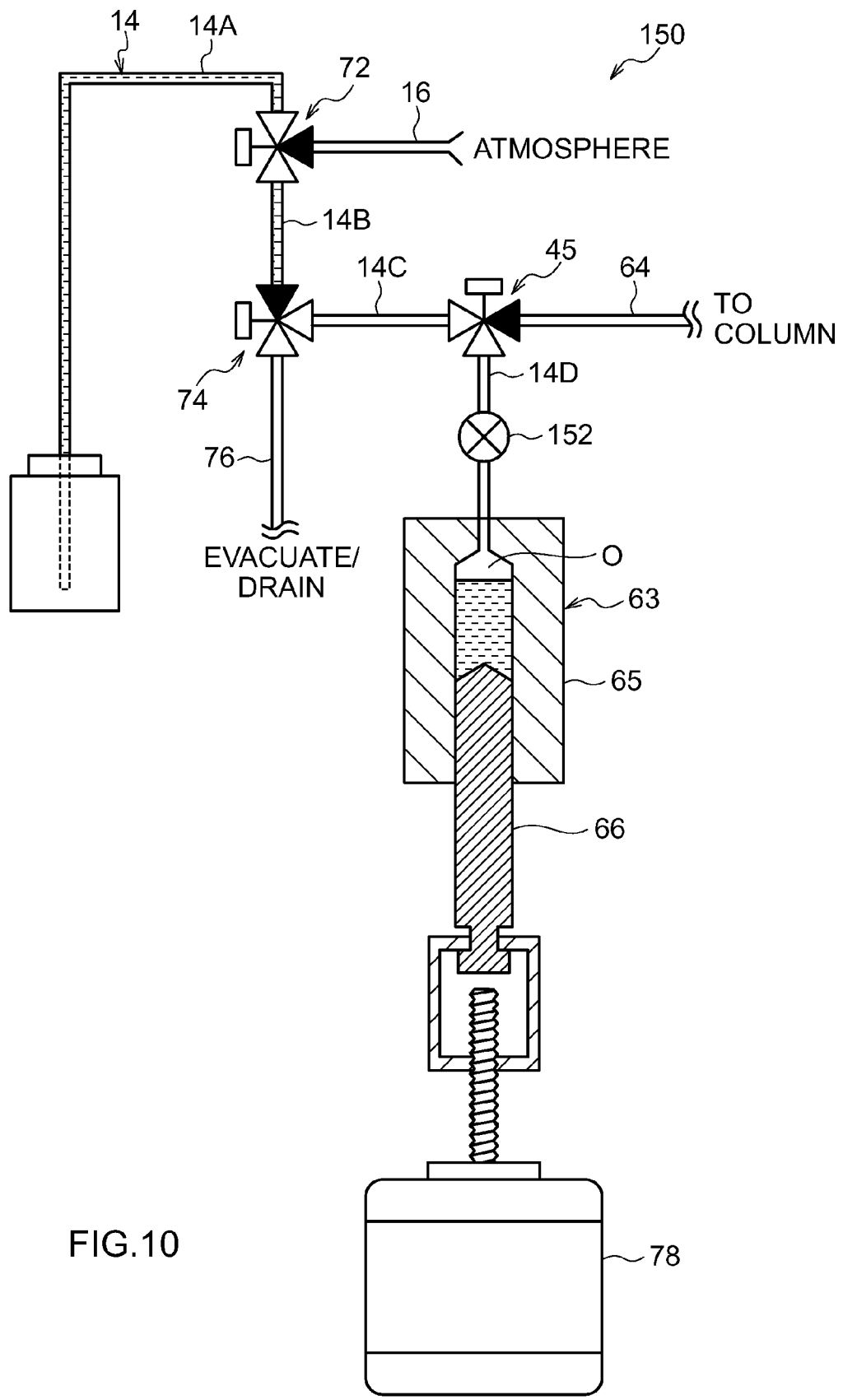
FIG. 10 is an enlarged diagram of principal portions, showing a bubble reduction device in accordance with a second exemplary embodiment.

Next, a bubble reduction device 150 according to a second exemplary embodiment of the present invention is described. Structures that are the same as in the first exemplary embodiment are assigned the same reference numerals and are not described here. As shown in FIG. 10, in the bubble reduction device 150 according to the present exemplary embodiment, a valve 152 is provided on the pipe 14D. The valve 152 differs from solenoid valves such as the first switching valve 74, simply opening and closing the pipe 14D. Other structures are the same as in the first exemplary embodiment.

Now, a procedure of degassing and supplying the eluent A with the plunger pump 63 in accordance with the present exemplary embodiment is described. The same as in the first exemplary embodiment, the air layer O is formed in the syringe 65 and the eluent A is sucked in by the procedure shown in steps 102 to 108 in FIG. 9. Thus, dissolved oxygen and bubbles in the eluent A come into contact with the air layer O and collect at the upper portion. Then, before the evacuation pipe 76 is opened in step 110, the control section 100 operates the valve 152 and the pipe 14D is closed, as illustrated in FIG. 10.

After the pipe 14D is closed, the control section 100 drives the motor 78 and the plunger 66 is pulled down. Thus, the volume of the interior of the syringe 65 increases and pressure is reduced in accordance with Boyle's law. As a result, dissolved oxygen remaining in the eluent A gasifies and is taken into the air layer O. Thereafter, the pipe 14D and the evacuation pipe 76 are opened and the air layer O is evacuated.

As described above, in the present exemplary embodiment the pressure in the syringe 65 is reduced separately from the operation of sucking in the eluent A. Therefore, the effectiveness of the degassing of dissolved oxygen may be raised.

Figure 13:
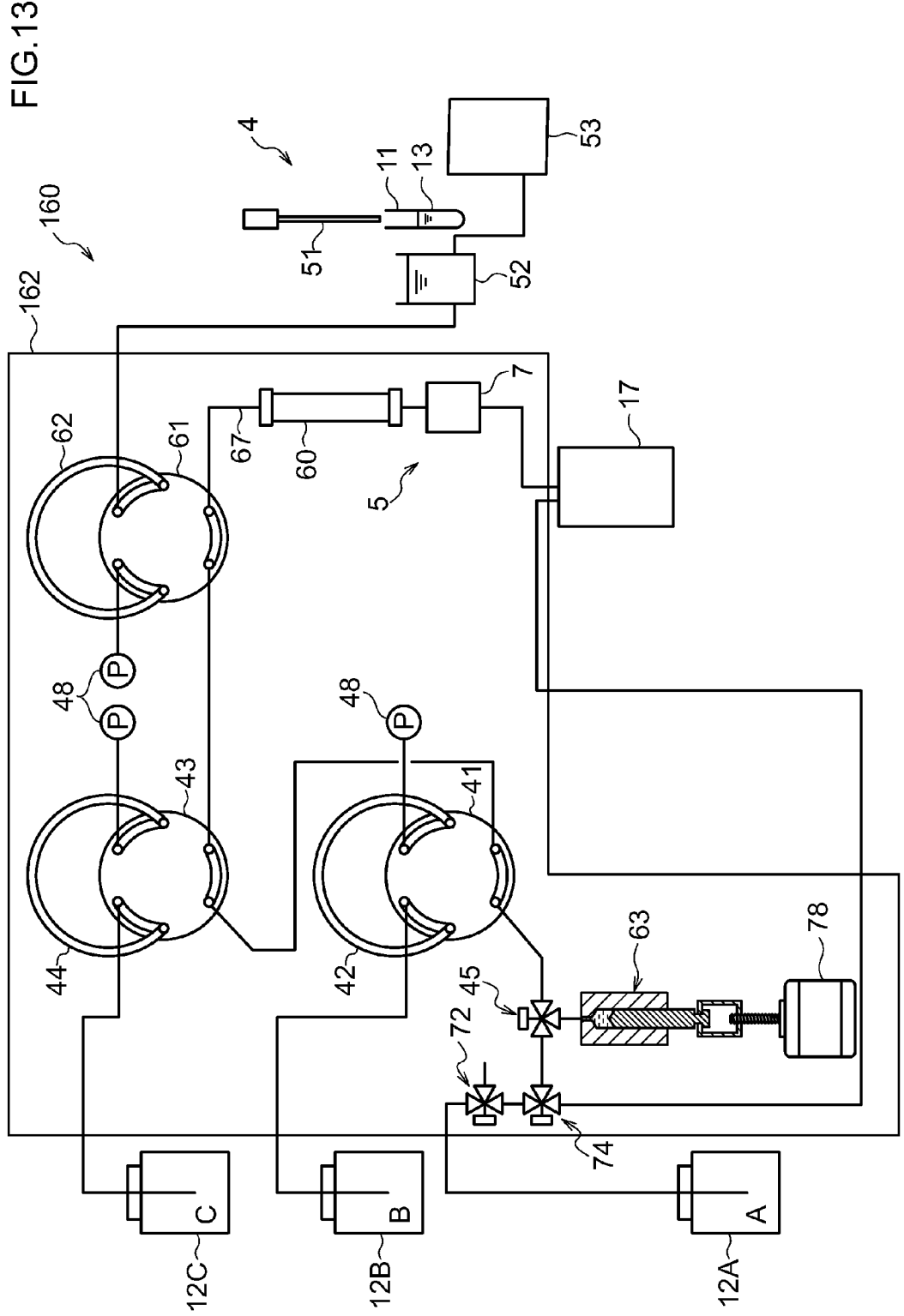
FIG. 13 is a schematic diagram showing internal structures of a chromatography device in accordance with a third exemplary embodiment.

Next, a chromatography device 160 according to a third exemplary embodiment of the present invention is described. Structures that are the same as in the first exemplary embodiment are assigned the same reference numerals and are not described here. As shown in FIG. 13, the chromatography device 160 according to the present exemplary embodiment is provided with a thermostatic tank 162.

The thermostatic tank 162 principally accommodates the plunger pump 63, atmosphere release valve 72, first switching valve 74, second switching valve 45, motor 78, switching valve 41, switching valve 43, switching valve 61, column 60 and photometry section 7 structuring the chromatography device 160. The internal temperature of the thermostatic tank 162 is maintained at a constant temperature. In the present exemplary embodiment, the eluent packs 12A, 12B and 12C, the sample preparation unit 4 and the waste liquid tank 17 are disposed at the outside of the thermostatic tank 162, but some or all of these may be accommodated in the thermostatic tank 162.

In the chromatography device 160 according to the present exemplary embodiment, the temperature of the thermostatic tank 162 is maintained at a temperature suitable for analysis. Thus, the degassing effect may be improved. For example, if the chromatography device 160 is installed in a room with a low temperature, there is more dissolved oxygen in an eluent. However, because the eluent is introduced into the interior of the thermostatic tank 162 and is warmed to the analysis temperature before the degassing processing, bubbles may be formed in the eluent beforehand. Thus, the degassing effect may be improved, in addition to which the formation of bubbles due to a temperature difference relative to the analysis unit 5 may be avoided.

A structure is also possible in which the channel between the eluent pack 12A and the plunger pump 63 is formed in a loop shape, the eluent A is sufficiently warmed while flowing along the loop-shaped channel, and is thereafter supplied to the plunger pump 63. The temperature of the interior of the thermostatic tank 162 may be freely specified in accordance with analysis components, the type of column 60 and the like.

Figure 14:
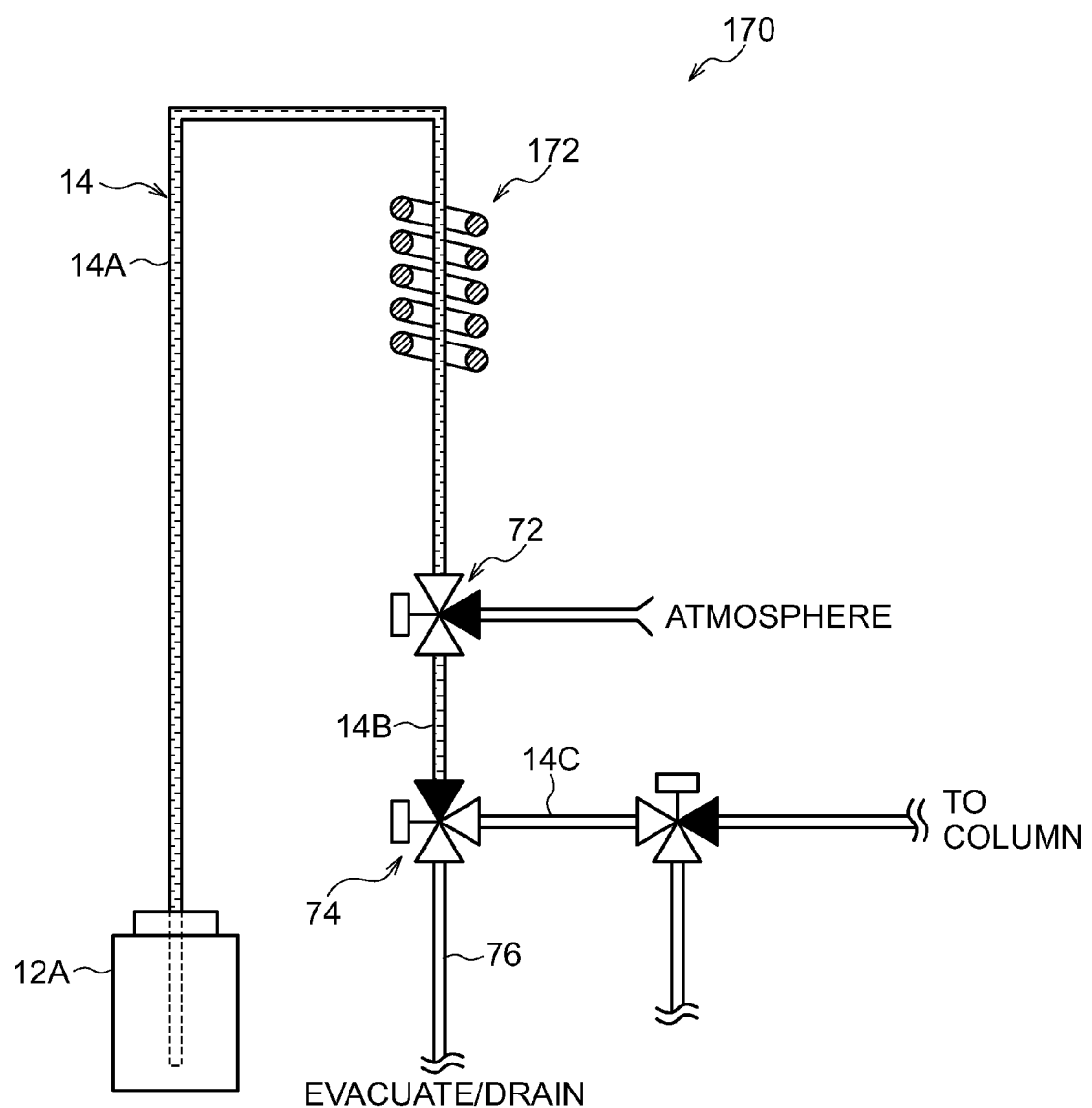
FIG. 14 is a schematic diagram showing a portion of a chromatography device in accordance with a fourth exemplary embodiment.

Next, a chromatography device 170 according to a fourth exemplary embodiment of the present invention is described. Structures that are the same as in the first exemplary embodiment are assigned the same reference numerals and are not described here. As shown in FIG. 14, the chromatography device 170 according to the present exemplary embodiment is provided with a heating coil 172 at the pipe 14A between the eluent pack 12A and the atmosphere release valve 72.

The heating coil 172 is formed in a coil shape wound round the pipe 14A. The heating coil 172 is connected to an electrical power supply. When power is supplied from the power supply to the heating coil 172, the eluent A flowing inside the pipe 14A is heated in accordance with the principle of induction heating.

Because the heating coil 172 as described above is used, the eluent A may be heated in a short time. Therefore, the eluent A may be warmed to an analysis temperature during the liquid suction step, and there is no need to separately provide a channel or the like for heat regulation. Moreover, because the eluent A is heated, oxygen dissolved in the eluent A forms bubbles and the bubbles may be efficiently removed at the plunger pump 63.

In the present exemplary embodiment, the eluent A is heated using the heating coil 172, but this is not limiting and other heating means may be employed. For example, a heated heater plate may press against and heat the pipe 14A.

Hereabove, the present invention has been described in accordance with the first to fourth exemplary embodiments, but the present invention is not limited by these exemplary embodiments. The exemplary embodiments may be used in combinations, and it will be clear that numerous modes may be embodied within a technical scope not departing from the spirit of the present invention. For example, in FIG. 4, the atmosphere release valve 72 may be provided on the pipe 14D to shorten the air introduction channel.

Further, the atmosphere release valve 72 may be not provided and the air layer O may be formed in the syringe 65 by another method. For example, a channel may be formed at the syringe 65 and put into fluid communication with the atmosphere. Further, the eluent A in the syringe 65 may be heated and large amounts of dissolved oxygen gasified to form the air layer O.

What is claimed is:

1. A liquid chromatography device comprising:
   a liquid accommodation portion that accommodates a liquid that is to elute an analysis component from a specimen adsorbed to an adsorption portion;
   a liquid supply apparatus that, by operation of a rod pushing up or pulling down, sucks or discharges the liquid through an aperture portion of a tube portion, the aperture portion being oriented upward;
   an air layer formation apparatus that forms an air layer in the tube portion;
   a first channel that connects the liquid supply apparatus with the liquid accommodation portion;
   a second channel that is connected to the first channel via a second switching valve, the second channel supplying the liquid discharged from the liquid supply apparatus to the adsorption portion;
   an evacuation portion that is connected to the first channel via a first switching valve and that evacuates the air layer through the first channel;
   an atmosphere release valve that is provided at at least one of the tube portion, the first channel or the second channel, and that introduces the air layer into the tube portion; and
   an analyzer that analyzes the analysis component in the liquid passed through the adsorption portion.

2. The liquid chromatography device according to claim 1, wherein the air layer formation apparatus includes an atmosphere release valve provided at the first channel, and
   the air layer is introduced into the tube portion through the first channel by an operation of the rod pushing up or pulling down in a state in which the atmosphere release valve is open.

3. The liquid chromatography device according to claim 1, wherein an upper portion inner wall of the tube portion tapers toward the aperture portion, and a distal end portion of the rod is formed in a shape similar to the shape of the upper portion inner wall.

4. A bubble reduction method comprising:
   a liquid accommodation step to accommodate a liquid into a liquid accommodation portion that is to elute an analysis component from a specimen adsorbed to an adsorption portion,
   a liquid supply step, which by pushing up or down a rod of the liquid supply apparatus, sucks or discharges the liquid from the liquid accommodation portion through an aperture portion of a tube portion, the aperture portion being oriented upward;
   a step to supply liquid discharged from the liquid supply apparatus to the adsorption portion, through which a first channel that connects the liquid supply apparatus with the liquid accommodation portion and a second channel that is connected to the first channel via a second switching valve, the second channel supplying the liquid discharged from the liquid supply apparatus to the adsorption portion;

an air layer formation step of forming an air layer in the tube portion and taking bubbles in the liquid into the air layer;

an evacuation step of evacuating the air layer in the tube portion through an evacuation portion that is connected to the first channel via a first switching valve and evacuates the air layer through the first channel;

a step to release the atmosphere through an atmosphere release valve that is provided at at least one of the tube portion, the first channel or the second channel, and that introduces the air layer into the tube portion; and an analyzing step to analyze using an analyzer that analyzes the analysis component in the liquid passed through the adsorption portion.

5. The bubble reduction method according to claim 4, wherein the liquid suction step includes pulling down a rod at a speed faster than a maximum movement speed of the liquid.

* * * * *